United States Patent [19]
Ohtomo et al.

[11] Patent Number: 5,509,420
[45] Date of Patent: Apr. 23, 1996

[54] BONE ASSESSMENT APPARATUS AND METHOD

[75] Inventors: Naoki Ohtomo; Shigeo Kimura, both of Tokyo, Japan

[73] Assignee: Aloka Co., Ltd., Mitaka, Japan

[21] Appl. No.: 268,187

[22] Filed: Jun. 29, 1994

[30] Foreign Application Priority Data

Jun. 30, 1993 [JP] Japan .................................. 5-162903

[51] Int. Cl.⁶ .................................................... A61B 8/00
[52] U.S. Cl. ......................................... 128/660.9; 73/644
[58] Field of Search .......................... 128/660.01, 660.03, 128/660.09, 660.06, 653.1, 661,03; 73/597, 644

[56] References Cited

U.S. PATENT DOCUMENTS

| | | |
|---|---|---|
| 3,847,141 | 11/1974 | Hoop . |
| 4,545,385 | 10/1985 | Pirschel ............................. 128/660.09 |
| 4,774,959 | 10/1988 | Palmer et al. . |
| 4,930,511 | 6/1990 | Rossman et al. . |
| 5,042,489 | 8/1991 | Wiener et al. . |
| 5,054,490 | 10/1991 | Rossman et al. . |
| 5,218,963 | 6/1993 | Mazess ............................... 128/660.06 |
| 5,348,009 | 9/1994 | Ohtomo et al. ..................... 128/653.1 |

OTHER PUBLICATIONS

Andre et al., "Measurement of the Velocity of Ultrasound in the Human Femur in Vivo",2389 Med. Phys. 7(4), Jul./Aug. 1980, p. 324–330.

*Primary Examiner*—George Manuel
*Attorney, Agent, or Firm*—Fish & Richardson

[57] ABSTRACT

A bone assessment apparatus for transmitting and receiving measuring waves through a test part of a patient to diagnose the condition of the test part, includes a measuring bath containing a coupling liquid required for precise measurement and an immersion pouch for keeping the test part out of contact with the coupling liquid. The test part is inserted into the immersion pouch in the measuring bath without touching the coupling liquid. Even during the screening of a number of patients the coupling liquid is prevented, from being contaminated by the test parts of the patients and therefore it is not necessary to change the coupling liquid often. The use of the immersion pouch is detected by a detector to correct a deviation in diagnosis data obtained from the received measuring wave on the basis of a specific correction value assigned to each immersion pouch, thereby providing more precise diagnosis data.

27 Claims, 5 Drawing Sheets

BONE ASSESSMENT APPARATUS AND METHOD

BACKGROUND OF THE INVENTION

1. Field of the Invention

This invention relates to a bone assessment apparatus and bone assessing method and more particularly to an apparatus and method for measuring physical parameters of a test part of a patient and computing data useful in diagnosing bone disorders by using measuring waves, such as an X-ray and an ultrasonic wave, transmitted and received through the test part.

2. Description of the Related Art

A bone assessment apparatus is disclosed in U.S. patent application Ser. No. 08/063,779 which can provide information useful for diagnosis of bone disorders through X-ray measurement or ultrasonic wave measurement. More specifically, physical parameters of a calcaneus or heel bone (hereinafter referred to as a test part), i.e. a bone mineral density calculated from an attenuation coefficient of an X-ray, and an ultrasonic wave propagation velocity, are obtained to compute a bone assessment index in order to determine whether or not the subject suffers from a bone disorder.

It is well known that, in transmitting and receiving an ultrasonic wave through a test part, an air layer existing between the ultrasonic transducers and the test part attenuates and reflects the ultrasonic waves, which degrades a measuring accuracy. For this reason, it has been performed to eliminate the air layer by filling the space between the transmitting/receiving devices and the test part with an acoustic matching material. Similarly, since X-rays are also attenuated if an air layer exists between the X-ray generator/detector and the test part, the air layer should be eliminated for keeping a measurement of precise bone mineral density. Thus, it has also been desired to provide a material equivalent to soft tissue such as skin or muscle between the test part and the transmitting/receiving devices.

In order to avoid the adverse affects of the air layer, a conventional apparatus has employed a bath containing water (preferably, distilled water containing a surface active agent) which functions both as a matching material for acoustic wave measurement and a soft tissue equivalent material for X-ray measurement. Then, the test part is immersed in the water, and ultrasonic waves and X-rays are irradiated through the water to the test part for measuring each of the physical parameters.

However, when a number of measurements are repeated by the conventional apparatus for many different patients, for example, at a mass checkup where only a primary diagnosis is made simply for deciding if the patient is suffered any bone disorder or not (this is called screening), many test parts are directly immersed in the coupling water in the bath, which quickly causes contamination of the water. Changing water at each time whenever a patient subject changes is not efficient.

SUMMARY OF THE INVENTION

This invention has been made to overcome the aforesaid problems in the conventional bone assessment apparatus. Therefore the object of the present invention is to realize an effective measurement without requiring a change of water by preventing the water from being contaminated even during a series of measurements of a number of patients.

In order to achieve the above objective, this invention provides a bone assessment apparatus using measuring waves irradiated to a test part, comprising devices for transmitting and receiving measuring waves through the test part, a measuring bath for containing a coupling liquid to exclude an air layer between the test part and the transmitting/receiving devices, and means for keeping the test part out of contact with the coupling liquid inside the measuring bath.

In another aspect of the invention, a bone assessment apparatus comprises devices for transmitting and receiving measurement waves through the test part, a measuring bath for containing a coupling liquid to exclude an air layer between the test part and the transmitting/receiving devices, a means removably provided in the measuring bath for keeping the test part out of contact with the coupling liquid, means for detecting the existence of the noncontacting means, and a data processor for computing diagnosis data based on the received measuring waves, said data processor being capable of correcting the diagnosis data computed from the received waves on the basis of a specific correction value assigned to each of the noncontacting means when the existence of the noncontacting means is detected by the detecting means.

According to a third aspect of the invention, a bone assessing method for transmitting and receiving measuring waves through a test part to diagnose the test part based on data obtained from the received waves, is also provided. This method comprises the steps of preparing a measuring bath filled with a coupling liquid, positioning the test part inside the measuring bath without contacting the coupling liquid, and transmitting and receiving the measuring waves through the test part.

The noncontacting means prevents a direct contact of the test part with the coupling liquid, which removes the necessity of changing the liquid due to contamination and realizes an efficient measurement even during a mass examination. The detecting means can detect a use of the noncontacting means, and the diagnosis data obtained from the measuring values is automatically corrected based on a specific correction value assigned to each of the noncontacting means. The noncontacting means is easily removable for quick change between a simple measurement with the noncontacting means and a precise measurement without the noncontacting means.

BRIEF DESCRIPTION OF THE DRAWINGS

The above and other objects, advantages and features of this invention will be more fully understood from the following detailed description in conjunction with the drawings, of which.

DESCRIPTION OF THE PREFERRED EMBODIMENTS

The preferred embodiments of the invention will now be described with reference to the drawings.

Figure 1:
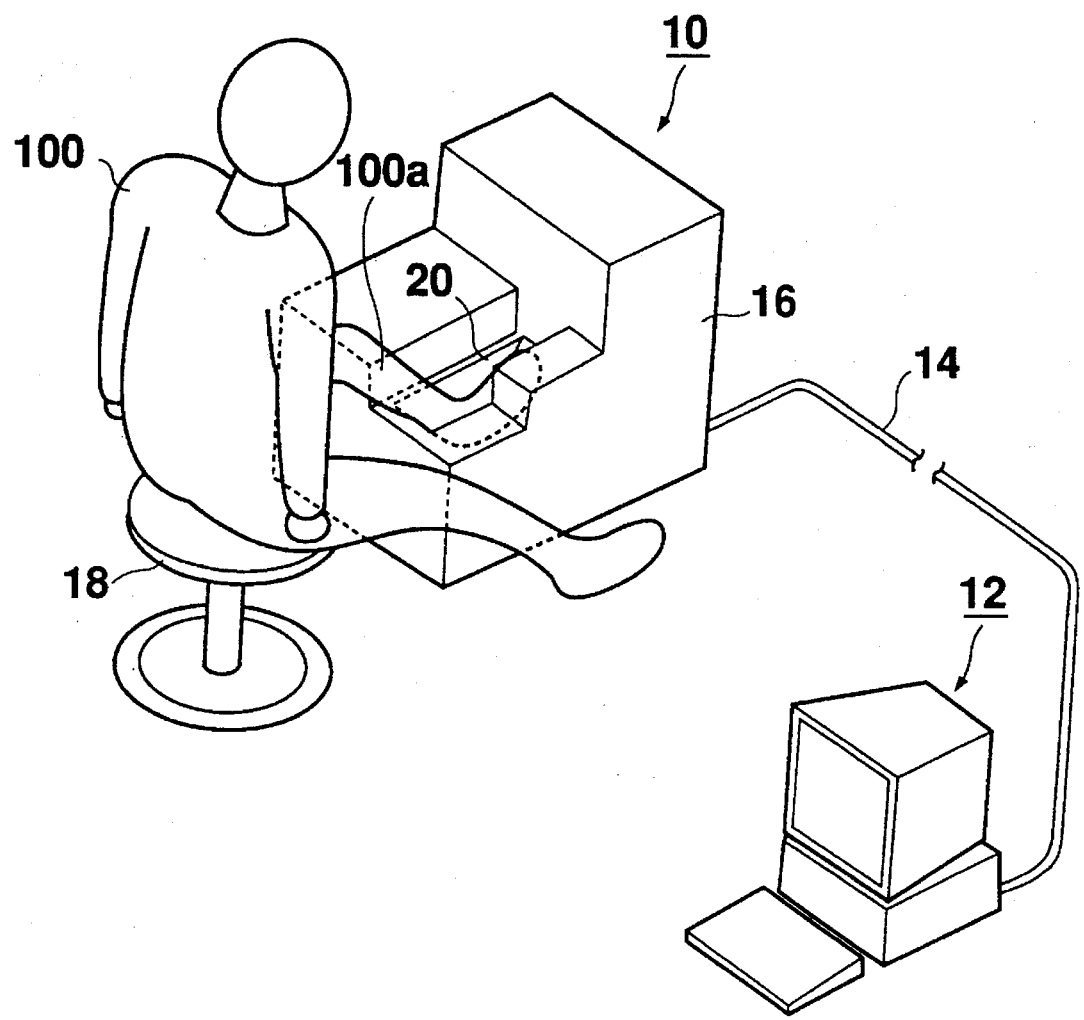
FIG. 1 is a schematic perspective view of an entire structure of the bone assessment apparatus.

In FIG. 1, an entire structure of a bone assessment apparatus is shown which includes a measuring apparatus 10 and a control unit 12. As shown in the figure, the control unit 12 consists of a computer unit which includes a data processor for computing diagnosis data on the basis of measuring waves received at wave-receiving devices which will be described in detail below. The control unit 12 is connected to the measuring apparatus 10 via a cable 14. The measuring apparatus 10 comprises a measuring unit 16 and a chair 18 which may be integrally or separately constructed with the measuring unit 16. The measuring unit 16 includes a measuring bath 22, which will be described below, arranged under an opening 20, and in the measuring bath 22, a foot rest for supporting a heel of a patient as a test part is positioned, which also serves as a positioning means for appropriately positioning the heel. In this embodiment, the foot rest is employed to support the heel for diagnosis of a calcaneus or heel bone.

During measurement, a patient 100 sits on the chair 18 and places his foot 100a onto the foot rest through the opening 20. In this situation, X-rays and ultrasonic waves, which are used as measuring waves, are irradiated and transmitted to the calcaneus.

Figure 2:
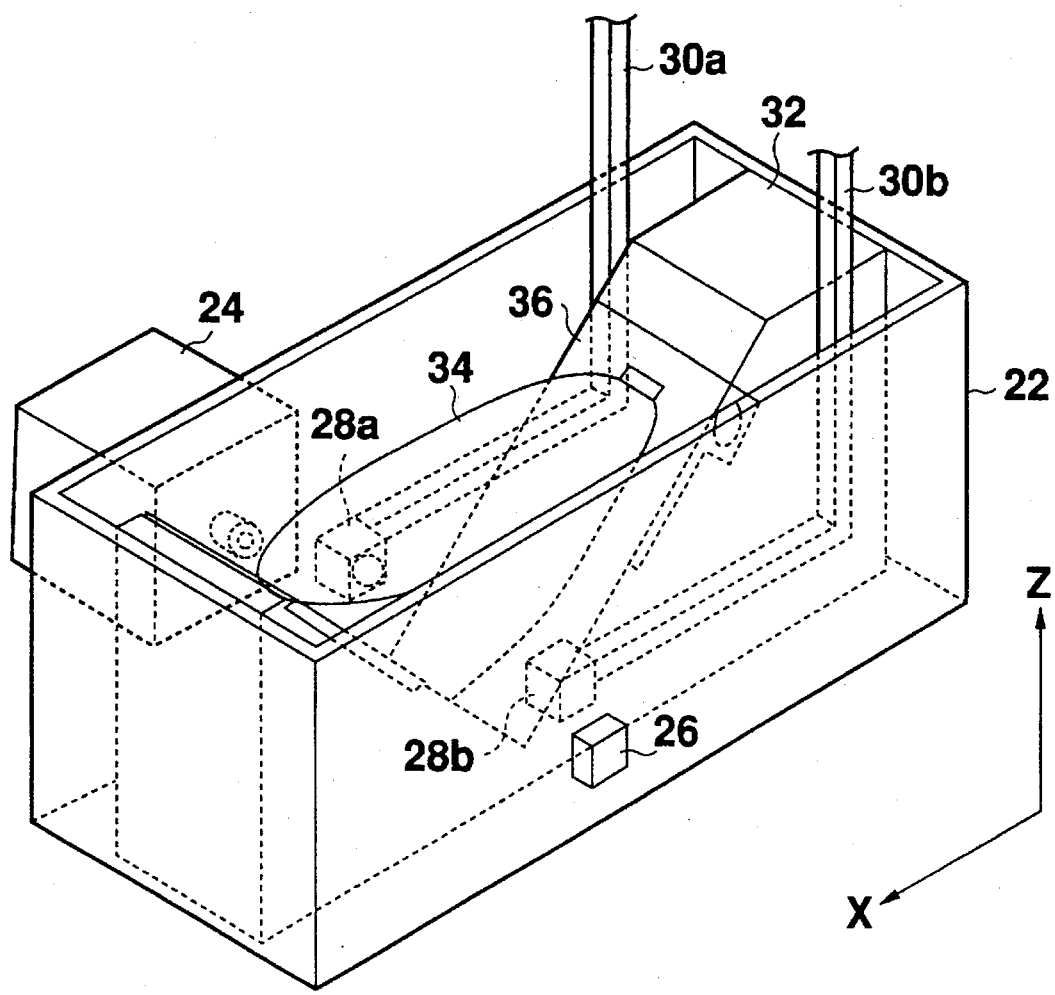
FIG. 2 is a schematic perspective view of a measurement bath.
Figure 3:
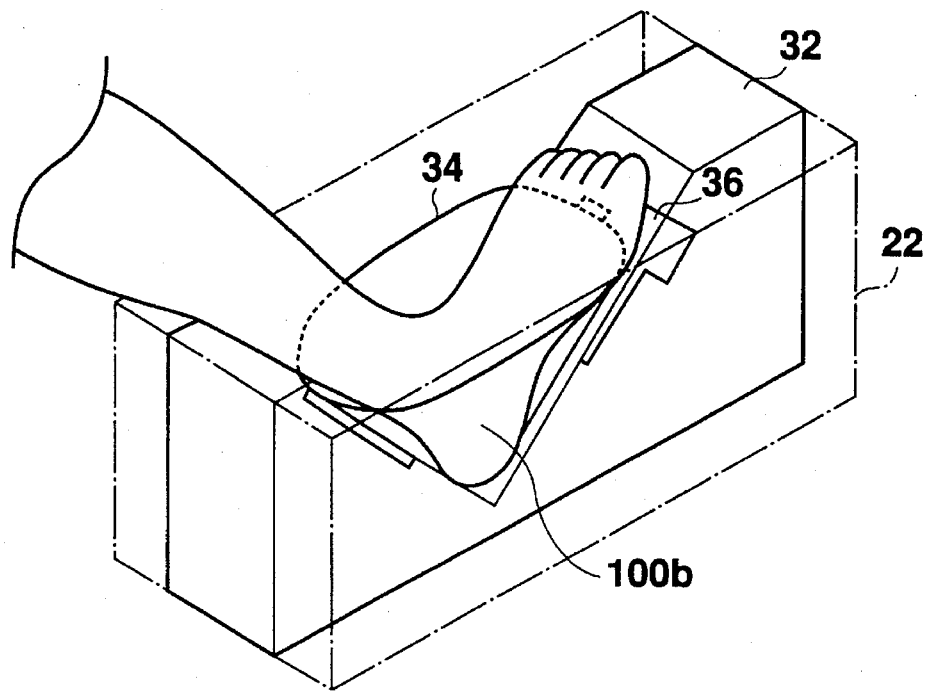
FIG. 3 illustrates a measuring condition of the bone assessment apparatus.

The measuring bath 22 is shown in FIG. 2, which is arranged under the opening 20 shown in FIG. 1. The measuring bath 22 contains water as coupling liquid which functions both as an acoustic matching material and a tissue-equivalent material required for measurement. The side walls of the bath 22 are made of, for example, an acrylic plate. The reason why the foot 100a should be immersed into the water is that the water has almost the same X-ray attenuation coefficient and acoustic wave propagation rate as those of a soft tissue. Thus, by filling the water in a space between the heel and the transmitting/receiving devices, the space can be considered as part of soft tissue. Under this condition, the boundary of soft tissue and the bone is clearly detected and an accurate measurement of bone mineral density can be achieved. Further, regardless of the volume or shape of soft tissue of the patient body, ultrasonic measurement can be performed accurately.

As shown in FIG. 2, an X-ray generator 24 and an X-ray detector 26 serving as a transmitter/receiver device are arranged outside the measurement bath 22, so as to be opposed to each other. The generator 24 and detector 26 can be moved on an X–Z plane by moving mechanism (not shown). Inside the measurement bath 22, ultrasonic transducers 28a and 28b are supported by arms 30a and 30b respectively, which serve as another transmitter/receiver device. These transducers 28a and 28b are also positioned on both sides of the heel so as to be opposed to each other. The arms 30a and 30b are driven by a transducer/arm moving mechanism (not shown) to move the ultrasonic transducers 28a and 28b on X–Z plane. As mentioned above, the foot rest 32 is positioned inside the measurement bath 22 for supporting the heel.

This invention is characterized in a noncontacting means for keeping the heel out of contact with the coupling liquid in the measuring bath 22. This noncontacting means is, for example, an immersion pouch 34 arranged inside the measuring bath 22. The immersion pouch 34 is removably attached by an attachment 36 onto the foot rest 32. This is very advantageous because a patient only inserts his heel 100b into the pouch 34 attached onto the foot rest 32 and a measurement is taken without contacting the water filling the measurement bath 22.

Figure 4:
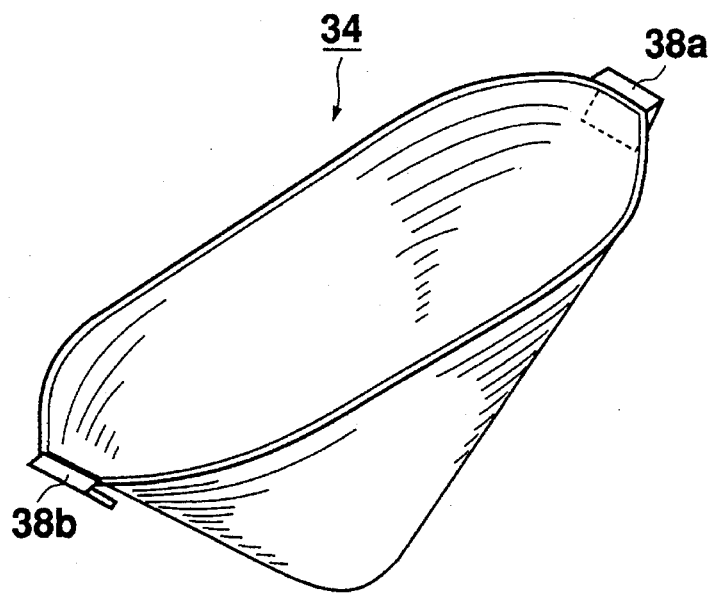
FIG. 4 is a perspective view of an immersion pouch according to the invention.

The immersion pouch 34 serving as the noncontacting means is shown in FIG. 4. The pouch 34 is made of, for example, a soft polyvinyl chloride. Thus, since the pouch material is so flexible as to easily fit to the shape of the patient's heel, an air layer between the heel and the inner wall of the pouch 34 is substantially eliminated, and the coupling liquid is prevented from flowing into the pouch 34. The hooks 38a,38b made of a hard polyvinyl chloride are provided on the upper edge of the immersion pouch 34, which are engaged with holes of the attachment 36 to attach the pouch 34. The immersion pouch 34 is sufficiently flexible to fit various shapes of patient's heels, as mentioned above. However, in order to ensure an acoustic matching between a patient's heel and the inner wall of the pouch 34, an acoustic matching jelly, which functions as a supplemental coupling agent, or a small quantity of water may be filled inside the pouch 34.

Figure 5:
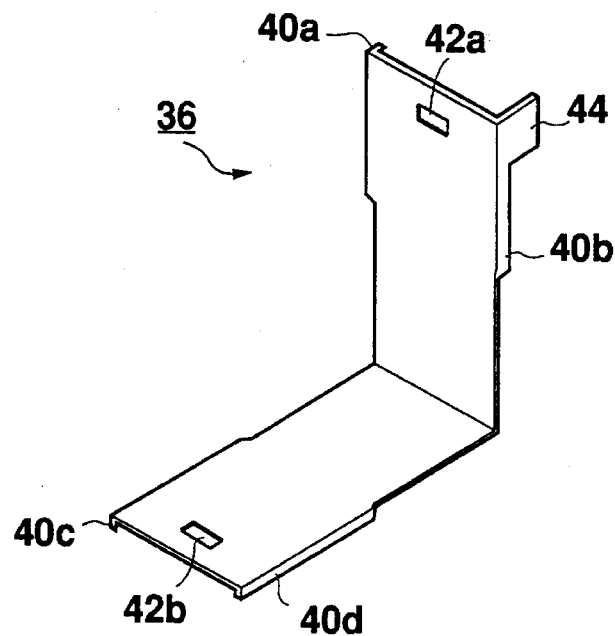
FIG. 5 is a perspective view of an attachment for attaching the pouch to the bone assessment apparatus.

FIG. 5 shows an attachment 36 which has a substantially L-shape with approximately 90 degrees between two supporting planes for supporting a heel in a natural manner inside the measuring bath 22. Guide flanges 40a, 40b, 40c, and 40d are formed along the longitudinal edge of the attachment 36, which are engaged with the edges of the foot rest 32, respectively. At each of the upper edges of the attachment 36, there are formed holes 42a, 42b to which the hooks 38a, 38b of the immersion pouch 34 are removably engaged, respectively. A blocking plate 44 is provided at a predetermined position on the attachment 36 for use in a detection of whether or not the immersion pouch 34 is used in measurement. In this embodiment, the blocking plate 44 is integrally formed with the guide flange 40b.

An actual operation of the bone assessment apparatus according to this embodiment will now be described.

When an operator intends to conduct a screening (i.e. preliminary measurement), he sets an attachment 36, to which an immersion pouch 34 is attached, onto the foot rest 32. A patient inserts his heel 100b into the immersion pouch 34 without directly touching the water filling the measuring bath 22. With this result, contamination of the water can be prevented. The operator inputs information from an input terminal of the control unit 12 for indicating that the measurement is carried out using an immersion pouch 34. In response to this command, the control unit 12 operates so as to correct a deviation caused by use of the immersion pouch 34 and to provide a more precise measurement result. The deviation is caused when the ultrasonic wave passes through the wall of the immersion pouch 34 having a different acoustic impedance from that of the water, before reaching the patient's heel. For example, if a thickness of the soft polyvinyl chloride pouch 34 is 0.05 mm, approximately 0.1% of deviation arises in the resultant value of propagation velocity of the ultrasonic wave. In this embodiment, such a deviation is corrected in advance in order to immediately provide a relatively accurate measurement result.

When the operator intends to make a more precise measurement of physical properties of the heel bone, he can easily remove the immersion pouch 34 by simply removing the attachment 36 and carry out a measurement without including any deviation caused by the immersion pouch 34.

Figure 6:
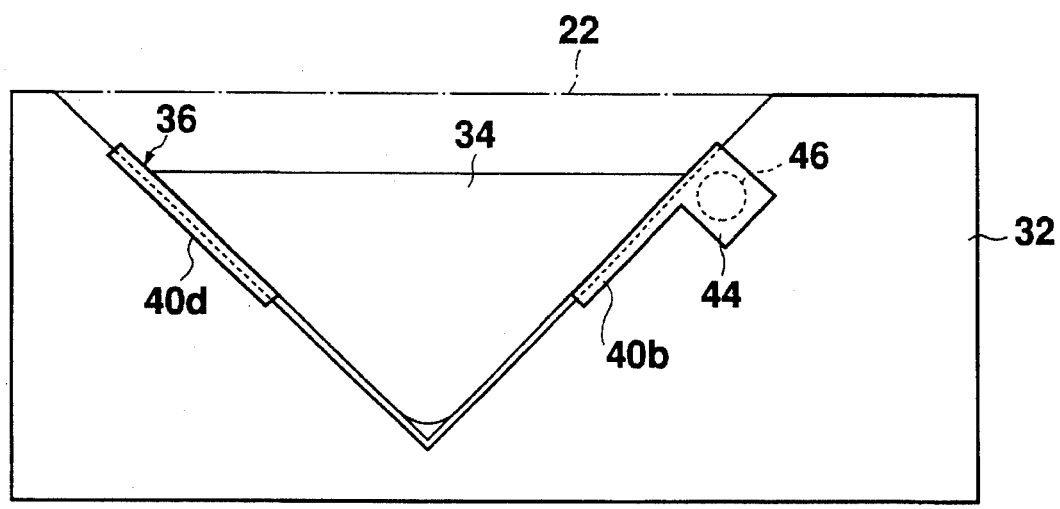
FIG. 6 is a schematic side view of the measurement bath where the immersion pouch is actually attached by an attachment to a foot rest.

The correction of the deviation can be automatically made when detecting the blocking plate 44 formed in the attachment 36. FIG. 6 shows the attachment 36 actually mounted on the foot rest 32. As shown in this figure, a through-hole 46 is formed on the side wall of the foot rest 32 so as to laterally penetrate the foot rest 32. When the attachment 36 is mounted on the foot rest 32, the blocking plate 44 of the attachment 36 covers the through-hole 46. Before the measurement, a detection of the existence of the blocking plate 44 is made by moving the ultrasonic transducers 28a, 28b to the position of the through-hole 46 and transmitting and receiving the ultrasonic wave at that position. In this manner, the blocking plate 44 and the ultrasonic transducers 28a, 28b construct a detecting means. If the existence of the immersion pouch 34 is detected, in response to the detection result, the control unit 12 automatically switches the operation mode of the bone assessment apparatus into a screening mode. Then, the control unit 12 sets measuring parameters and processes so as to be suitable for screening, and corrects resultant diagnosis data on the basis of a predetermined correction value. The pouch detecting means may be constructed with another type of sensor, such as infrared sensor or magnetic sensor.

The through-hole 46 may be used for detecting a suitable water level filling the measuring bath 22, as is disclosed in Japanese Patent Application No. H5-45161.

Although the invention has been described with reference to a specific example, this is not limited to the embodiment. For example, although, in the embodiment, a soft polyvinyl chloride is used for the immersion pouch which should be flexible and fittable to a heel shape, another material such as an elastic rubber may be used. Further the pouch can be constructed to fit a toe shape.

Figure 7:
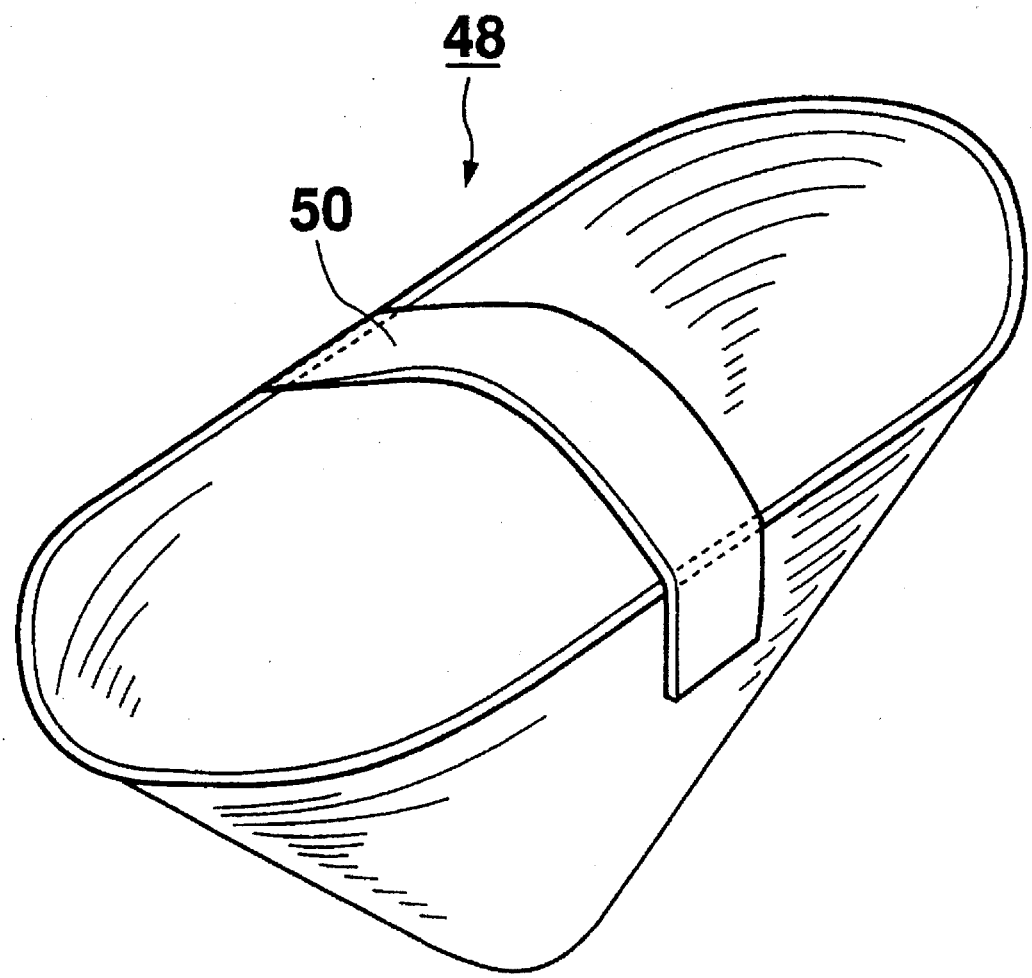
FIG. 7 is a perspective view of another embodiment of the immersion pouch.

Further, the immersion pouch is not necessarily attached via the attachment. For example, as shown in FIG. 7, a band 50 is provided to the upper opening of the pouch 48 to retain an ankle of a patient. In this case, the pouch 48 is used like a shoe, and the patient can put on the pouch 48 before immersing his foot in the water.

The immersion pouches 34, 48 shown in FIGS. 4 and 7 are used as an auxiliary member for a bone assessment apparatus. These pouches may be disposable.

The bone assessment apparatus of the invention is generally used for diagnosing physical properties of tissue by using an ultrasonic measurement and X-ray measurement, but can be applied to various apparatus as long as they utilize transmission/reception of ultrasonic wave and irradiation of X-ray directed to a test part of a patient which is immersed in a coupling liquid or the like.

What is claimed is:

1. A bone assessment apparatus for transmitting and receiving measuring waves through a test part of a patient to diagnose the test part based on data obtained from the received waves, comprising:

transmitting/receiving devices for transmitting and receiving measuring waves through the test part;

a measuring bath for containing a coupling liquid to exclude an air layer between the test part and the transmitting/receiving devices; and noncontacting means for keeping the test part out of contact with the coupling liquid inside said measuring bath.

2. A bone assessment apparatus according to claim 1, wherein said noncontacting means for keeping the test part out of contact with the coupling liquid includes an immersion pouch for receiving the test part.

3. A bone assessment apparatus according to claim 2, wherein said immersion pouch is removably attached inside the measuring bath for receiving the test part.

4. A bone assessment apparatus according to claim 3, further comprising means for positioning the test part to a predetermined measuring position where the measuring waves are appropriately transmitted and received through the test part.

5. A bone assessment apparatus according to claim 4, wherein said positioning means includes a rest for supporting the test part and is located inside the measuring bath.

6. A bone assessment apparatus according to claim 5, wherein said test part is a heel of the patient and said rest has a L-shaped portion for supporting the heel.

7. A bone assessment apparatus according to claim 5, further comprising an attachment means for removably attaching the immersion pouch to the test part supporting rest.

8. A bone assessment apparatus according to claim 7 wherein said attachment means comprises an attachment engaging with the rest, and hooks provided on the immersion pouch for engaging with the attachment.

9. A bone assessment apparatus according to claim 8, wherein said hooks are made of hard polyvinyl chloride.

10. A bone assessment apparatus according to claim 4, wherein said immersion pouch has such shape and size that dose not allow the coupling liquid to flow into the pouch and is fitting to the test part when the test part is held at the predetermined measuring position of the positioning means.

11. A bone assessment apparatus according to claim 2, wherein said immersion pouch is made of a flexible plastic material fitting the test part.

12. A bone assessment apparatus according to claim 11, wherein the immersion pouch is made of soft polyvinyl chloride.

13. A bone assessment apparatus according to claim 2, wherein said immersion pouch can be removably attached to the test part before being immersed in the measuring bath.

14. A bone assessment apparatus according to claim 13, wherein said immersion pouch has a band for retaining the test part.

15. A bone assessment apparatus according to claim 1, wherein said measuring waves are an ultrasonic wave and an X-ray.

16. A bone assessment apparatus for transmitting and receiving measuring waves through the test part to diagnose the test part based on data obtained from the received wave, comprising:

transmitting/receiving devices for transmitting and receiving measuring waves through the test part;

a measuring bath for containing a coupling liquid to exclude an air layer between the test part and the transmitting/receiving devices;

noncontacting means removably provided in the measuring bath for keeping the test part out of contact with the coupling liquid;

means for detecting the existence of the noncontacting means; and a data processor for computing diagnosis data based on the received measuring waves, said data processor being capable of correcting the diagnosis data computed from the received wave on the basis of a specific correction value assigned to each of the noncontacting means, when the existence of the noncontacting means is detected by the detecting means.

17. A bone assessment apparatus according to claim 16, wherein said detecting means has a blocking plate on the propagation path of the measuring wave for blocking the measuring wave, whereby detecting the existence of the noncontacting means based on whether or not the measuring wave is blocked by the blocking plate.

18. A bone assessment apparatus according to claim 17, wherein said measuring wave to be blocked by the blocking plate is an ultrasonic wave.

19. A bone assessing method for transmitting and receiving measuring waves through a test part to diagnose the test part based on data obtained from the received waves, comprising the steps of:

preparing a measuring bath filled with a coupling liquid;

positioning the test part inside the measuring bath without contacting the coupling liquid;

transmitting and receiving the measuring waves through the test part.

20. A bone assessing method according to claim 19, wherein said positioning step includes a step of inserting the test part into an immersion pouch which has been attached inside the measuring bath, and said transmitting/receiving step includes a step of transmitting and receiving the measuring waves through the test part via the immersion pouch.

21. A bone assessing method according to claim 20, further comprising a step of filling the immersion pouch with a small quantity of supplemental coupling agent.

22. A bone assessing method according to claim 20, wherein said immersion pouch is fitted to the test part in advance of being immersed in the measuring bath, and the measuring waves are transmitted and received via the immersion pouch.

23. A bone assessing method according to claim 22, further comprising a step of filling the immersion pouch with a small quantity of supplemental coupling agent.

24. An auxiliary member for use in a bone assessment apparatus in which a heel of patient is immersed in a measuring bath filled with a coupling liquid and measuring waves are irradiated to the heel for diagnosing a bone disorder, said auxiliary member being used for keeping the heel out of contact with the coupling liquid, and the auxiliary member including an immersion pouch having high plasticity fitting to the heel.

25. An auxiliary member according to claim 24, which has been removably attached inside the measuring bath for receiving the heel.

26. An auxiliary member according to claim 24, which can be fitted to the heel in advance of being immersed in the measuring bath.

27. A bone assessment apparatus comprising:

a measuring bath containing a coupling liquid into which a heel of a patient is adapted to be immersed for diagnosis;

Ultrasonic wave and X-ray measuring devices for irradiating an ultrasonic wave and an X-ray to the heel of the patient to perform a measurement of a bone strength; and means removably provided in the measuring bath for keeping the heel out of contact with the coupling liquid inside the measuring bath.

* * * * *